United States Patent [19]

Katz et al.

[11] Patent Number: 4,539,698
[45] Date of Patent: Sep. 3, 1985

[54] REPLACEABLE SALIVA BARRIER FOR INTRA-ORAL LARYNX

[75] Inventors: Philip Katz, Princeton Junction; Henry S. Brenman, Cinnaminson, both of N.J.; Louis D. Lowry, Villanova; Harold Schwartz, King of Prussia, both of Pa.

[73] Assignee: Thomas Jefferson University, Philadelphia, Pa.

[21] Appl. No.: 547,740

[22] Filed: Nov. 1, 1983

Related U.S. Application Data

[63] Continuation-in-part of Ser. No. 438,376, Nov. 1, 1982, and Ser. No. 428,848, Sep. 30, 1982, Pat. No. 4,502,150, which is a continuation of Ser. No. 249,140, Mar. 30, 1981, Pat. No. 4,473,905, said Ser. No. 438,376, is a continuation-in-part of Ser. No. 249,140, Mar. 30, 1981.

[51] Int. Cl.$^3$ .............................................. A61F 1/20
[52] U.S. Cl. ......................................... 381/70; 3/1.3
[58] Field of Search ............................... 381/70; 3/1.3

[56] References Cited

U.S. PATENT DOCUMENTS

| | | | |
|---|---|---|---|
| 2,093,453 | 9/1937 | Kellotat | 3/1 |
| 2,862,209 | 12/1958 | Cooper | 381/70 |
| 3,072,745 | 1/1963 | Barney | 179/1 |
| 3,084,221 | 4/1963 | Cooper | 381/70 |
| 3,291,912 | 12/1966 | Flanagan | 179/1 |
| 3,508,000 | 4/1970 | Snyder | 179/1 |
| 3,766,318 | 10/1973 | Webb | 179/1 |
| 3,914,550 | 10/1975 | Cardwell, Jr. | 179/1 |
| 4,039,756 | 8/1977 | Burtschi | 179/1 |
| 4,223,411 | 9/1980 | Schoendorfer et al. | 3/1.3 |

FOREIGN PATENT DOCUMENTS

| | | |
|---|---|---|
| 208505 | 4/1960 | Austria . |
| 0058077 | 8/1982 | European Pat. Off. . |
| 2507704 | 9/1976 | Fed. Rep. of Germany . |
| 2515006 | 10/1976 | Fed. Rep. of Germany . |
| 2818853 | 11/1978 | Fed. Rep. of Germany . |
| 1213521 | 11/1970 | United Kingdom . |
| 1592872 | 7/1981 | United Kingdom . |

OTHER PUBLICATIONS

Goode et al., "An Intraoral RF Powered Artificial Larynx", Proceedings of the 23rd Annual Conference on Engineering in Medicine & Biology—Washington, D.C., 1970, vol. 12, p. 335.

Medorobics, Inc., publication distributed at International Association for Laryngectomees Annual Convention, Wichita, Kans., summer, 1982.

Schoendorfer et al., "The Development of an Internally Worn Vocal Prosthesis", *J. of Clinical Engineering*, 4:29-38, No. 1, Jan.-Mar. 1979, (Quest Pub. Co.).

"An Electrical Vocal System", L. O. Schott, Bell Laboratories Record, Dec. 1950, pp. 549-555.

"The Calculation of Vowel Resonances, and an Electrical Vocal Tract", H. K. Dunn, *Journal of the Acoustical Society of Amer.*, 22:740-753, No. 6, Nov. 1950.

(List continued on next page.)

*Primary Examiner*—Gene Z. Rubinson
*Assistant Examiner*—W. J. Brady
*Attorney, Agent, or Firm*—Woodcock Washburn Kurtz Mackiewicz & Norris

[57] ABSTRACT

An intra-oral artificial larynx is provided including a signal generator and a speaker mounted on a prosthesis for mounting the larynx within the intra-oral cavity. A horn is provided having an input opening coupled to the speaker for acoustically amplifying the output of the speaker, the horn also having an output opening. A saliva barrier is removably mounted to the output opening of the horn for precluding penetration of saliva into the horn, the barrier having a first end which is telescopically received within the output opening of the horn and the second end having a mouth formed on a bias to the longitudinal axis of the mounting and a microporous membrane sealing the mouth. The mouth of the mounting has an elliptical shape which has been found tends to increase speaker volume. Moreover, the telescopic mating of the mounting and the horn provides a saliva barrier which is easily replaceable by the user.

3 Claims, 7 Drawing Figures

OTHER PUBLICATIONS

"An Electrical Analog of the Vocal Tract", K. N. Stevens et al., *Journal of the Acoustical Society of America*, 25:734–742, No. 4, Jul. 1953.

"The Use of the Manufactured Larynx for Alaryngeal Speech Training", Shanks, Therapy for the Laryngectomized Patient, Rigrodsky et al., Teachers College Press, 1971, Chapter 5, pp. 53–66.

"Biophysical Requirements for New and Projected Procedures and Devices for Voice Rehabilitation After Total Laryngectomy", Murry, Canadian Journal of Otolaryngology, 4:4, 1975, pp. 571–578.

"The Artificial Larynx: Types, Applications and Modifications", Blom Audiology-Speech Pathology Service, Veterans Administration Hospital, Indianapolis, Ind.

"Artificial Laryngeal Devices in Post-Laryngectomy Rehabilitation", Goode, Centennial Conf. on Laryngeal Cancer, Toronto, Can., 5/28/74, pp. 677–689.

"Development and Testing of an Intraoral Electrolarynx for Laryngectomy Patients", Zitman et al, J. of Speech and Hearing Disorders, XLIII, May 1978, pp. 263–269.

"A Modified Intraoral Electrolarynx", McRae et al, Arch Otolaryngol, vol. 105, Jun. 1979, pp. 360–361.

"A Self-Contained Intra-Oral Artificial Larynx", by Kenneth J. Stern, Bioengineering Senior Design Project-Be-495, Fall, 1978, Spring, 1979, (43 pages).

"A Self Contained Intra-Oral Artificial Larynx", B.E. 495, Senior Design Project, Kenneth Stern, (7 pages).

"A Self Contained Intra-Oral Electro-Larynx", Progress Report, Dec. 1979, Kenneth Stern Bioengineering 495 Senior Design Project, (16 pages).

Knorr et al., "The Design of a Wireless-Controlled Intraoral Electro-larynx", *Journal of Bioengineering*, 1: 165–171, 1977.

Katz et al., "A Self-Contained Intraoral Artificial Larynx", *Proc. ASHA*, Nov. 1981.

Katz et al., "A Clinical Device for Revocalization of the Laryngectomized Patient", *IEEE Fron. Eng. Health Care*, 318–320, Sep. 1981.

Lowry et al., "An Intraoral Artificial Larynx", *Trans. Am. Acad. Oto*, 1981.

"Artificial Larynx... Spotting Diabetes... Anti-Acne Drug", *U.S. News & World Report*, p. 75, Sep. 28, 1981.

"Flicks of the Tongue Operate Artificial Larynx on Dental Plate", Medical World News, p. 38, Sep. 1, 1981.

"Intraoral Artificial Larynx Developed at Jefferson", *Philadelphia Medicine*, vol. 77, No. 9, Sep. 1981, p. 377.

"Mini Voice-Box", *Discover*, p. 78, Sep. 1981.

"Electronic Age Brings New Aids for the Disabled, but Economics Put Them Out of Reach of Many", *The Wall Street Journal*, Aug. 26, 1980, p. 52.

"Doctors Develop Self-Contained Voicebox", *Bulletin*, Providence, R.I., Jul. 13, 1981.

"Doctors Develop New-Type Artificial Voicebox", *Herald*, Provo, Utah, Jul. 16, 1981.

"Doctors Hope Voicebox Will End 'Social Stigma'", *Patriot Ledger*, Quincy, Mass., Jul. 13, 1981.

"Throat Patients to Get Artificial Voice", *Star*, Sep. 15, 1981.

"Jeff Team Invents Intraoral Artificial Larynx", *Directions*, Jun. 1981.

"First Self-Contained Voicebox Developed", *Standard Examiner*, Ogden, Utah.

"New Artificial 'Voicebox' Fits into Mouth", Montgomery County *Post*, Jul. 29, 1981, p. 23.

"Researchers Develop First Intraoral Artificial Larynx", *ASHA*, Sep. 1981.

"It's A Medical First: After Larynx Surgery an Electronic Voice", *The Bulletin*, Jul. 5, 1981, p. 1–B.

"New Artificial Larynx is Invisible", *Daily Local News*, Aug. 4, 1981.

Lowry, "Voice Box in the Mouth", *Science Digest*, Nov. 1981.

REPLACEABLE SALIVA BARRIER FOR INTRA-ORAL LARYNX

RELATED APPLICATIONS

This application is a continuation-in-part of Ser. No. 438,376, filed Nov. 1, 1982 which is, in turn, a continuation-in-part of Ser. No. 249,140 filed Mar. 30, 1981, now U.S. Pat. No. 4,473,905, and is also a continuation-in-part of Ser. No. 428,848 filed Sept. 30, 1982, now U.S. Pat. No. 4,502,150, which, in turn, is a continuation of the said Ser. No. 249,140 filed Mar. 30, 1981, now U.S. Pat. No. 4,473,905 all of which are incorporated herein by reference as if fully set forth in full.

BACKGROUND OF THE INVENTION

The present invention relates, in general, to the field of sound producing prosthetic devices for use by laryngectomized patients, and in particular, relates to a self-contained intra-oral artificial larynx and an improved saliva barrier therefor.

Many devices have been suggested for providing speech capability to laryngectomized patients. The most successful and important of these devices known to the present applicants is the artificial larynx described in detail in the immediate parent application to the present application, i.e., application Ser. No. 438,376, filed Nov. 1, 1982. In that application, various prior art techniques of artificially producing speech by a laryngectomized patient are discussed. Unlike the prior art devices which had relied upon extra-oral components, the device disclosed and claimed in the parent application is one which resides entirely within the mouth of the patient and which is incapable of visual detection.

The device disclosed and claimed in the parent application includes, inter alia, a power source, a signal generator, a speaker, an acoustic horn and a tongue activated switch, all of which are mounted to a dental prosthesis and situated within the wearer's mouth. All of the aforementioned components, as well as others, are formed in the body of a dental prosthesis which is formed of conventional dental prosthetic materials, such as an acrylic polymer, which is shaped to fit comfortably against the roof of the wearer's mouth. Upon activation of the switch, the signal generator disclosed in the immediate parent application to the present application produces an electrical signal. The electrical signal is converted to acoustic energy by the speaker. The acoustic energy emanating from the speaker is amplified by an acoustic horn. As disclosed in the parent application, it is undesirable for saliva to enter the horn since saliva may foul the speaker. Accordingly, in the immediate parent application to the present application, a porous saliva barrier is disclosed which prevents the penetration of saliva into the acoustic horn.

It has been found, however, that even this porous saliva barrier may become fouled with saliva thus rendering the larynx inoperative or at a minimum, greatly reducing the output volume of the device. In the immediate parent application to the present application, a saliva barrier is disclosed which is permanently attached to the larynx.

It would be desirable to provide a saliva barrier for an intra-oral artificial larynx which is removable and replaceable without destruction of the larynx itself.

It would be further desirable to provide an intra-oral artificial larynx which includes a saliva barrier which is removable such that periodic replacement can occur.

It is still further desirable to provide an intra-oral artificial larynx in which output volume is maximized.

SUMMARY OF THE INVENTION

These and other objects of the present invention are met by the provision of an intra-oral artificial larynx including a prosthesis for mounting the larynx within the intra-oral cavity, a signal generation means mounted on the prosthesis for generating a preselected electrical signal and a speaker mounted on the prosthetic means for converting the signal into acoustic energy. A horn having an input opening coupled to the speaker acoustically amplifies the output of the speaker. The horn includes a microporous barrier removably mounted to the output opening of the horn for precluding the penetration of saliva into the horn.

In accordance with one aspect of the present invention, the barrier means includes a saliva barrier cartridge which is removably mounted to the output opening of the horn. The cartridge includes a mounting having a central opening in acoustic communication with the output opening of the horn and a microporous membrane sealing that central opening.

The provision of a saliva barrier cartridge permits the replacement of the saliva barrier as necessary by the patient.

BRIEF DESCRIPTION OF THE DRAWINGS

The present invention will be more fully understood by reference to the accompanying drawings in which.

DETAILED DESCRIPTION OF THE PREFERRED EMBODIMENT

Figure 1:
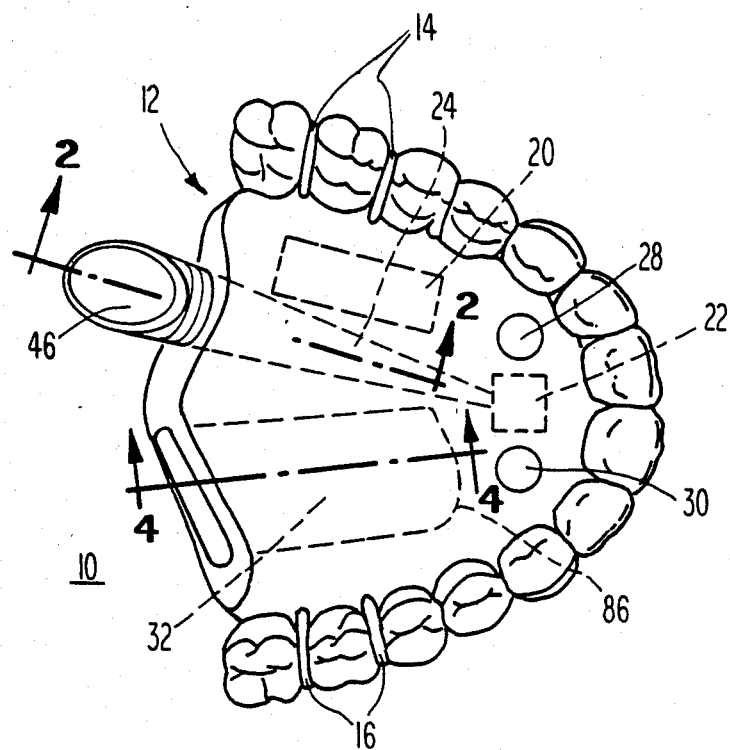
FIG. 1 is a diagrammatic plan view of the bottom surface of a preferred embodiment of an artificial larynx, illustrating the speaker, acoustic horn, tongue contacts, circuitry and power source within an otherwise conventional dental prosthesis.

Referring now to FIG. 1, the intra-oral artificial larynx of the present invention will be seen generally at 10. As shown in FIG. 1, the larynx 10 is shown in position against the roof of the intra-oral cavity of the patient. The larynx of FIG. 1 comprises a prosthetic means, designated generally at 12, which comprises a conventional, palatal denture or dental prosthesis. Such a prosthesis usually comprises a means for anchoring the prosthesis in the mouth cavity; such means in FIG. 1 being dental wires 14 and 16. The body 18 of the dental prosthesis 12 is formed from conventional dental prosthetic materials, such as an acrylic polymer, which is shaped to fit against the roof of the mouth. The body 18 of the prosthesis is preferably formed to encapsulate all of the electrical components of the preferred embodiment of the larynx. Specifically, the body 18 encapsulates a signal generating circuit 20 for generating a preselected electrical signal. It also encapsulates a speaker 22 for converting the signal into acoustic energy. The body 18 of the molded prosthesis 12 also encapsulates an acoustic horn 24 which is the preferred acoustic amplification means for amplifying acoustic energy generated by the speaker 22. As shown in FIG. 1, the preferred acoustic horn 24 is conical, having its minimum diameter at its juncture with the speaker 22 and its maximum diameter at its terminus 26 at the rear of the prosthesis 12.

The larynx 10 of the present invention is controlled by switches 28 and 30 pressed with the tongue. As is described more fully hereinafter, the touching of either of these switches 28 or 30 acts to complete a ground path in the larynx.

The efficiency of the sound circuitry of the present invention makes it possible to use a low voltage, low current power source. The power source is situated in a power source compartment 32 which is formed in the body 18 of the prosthesis by a method to be described below. For the embodiment of FIG. 1, the power source may comprise lithium, silver oxide or nickel cadmium or other rechargeable type batteries recharged by any means.

Special precautions are taken to prevent the speaker 22 from becoming fouled with water or saliva. In addition to increasing the amplitude of the sound generated by the speaker 22, the acoustic horn 24 aids in protecting the speaker 22 from liquids contained within the mouth. This protection results from the location of the speaker at the extreme proximate end of the horn. Additional protection against flooding of the speaker 22 may be attained by covering the mouth 26 of the horn 24 with a thin sheet of material which will prevent liquids from entering the horn but which will permit water vapor and air to pass therethrough. Hydrophobic, microporous material such as polytetrafluoroethylene sheets (half mil) sold under the tradename "Teflon FEP fluorocarbon film" by American Durafilm Company, Inc. of Newton, Lower Falls, Mass., are suitable for this purpose.

The microporous saliva barrier must be replaced periodically by the patient. In accordance with one aspect of the present invention, the saliva barrier is fixed to a removable saliva barrier cartridge which, in turn, is removably attached to the mouth 26 of the horn 24. In this manner, the saliva barrier cartridge may be prepackaged and is disposable such that replacement of the microporous saliva barrier membrane may be accomplished readily, even by handicapped patients.

Figure 2:
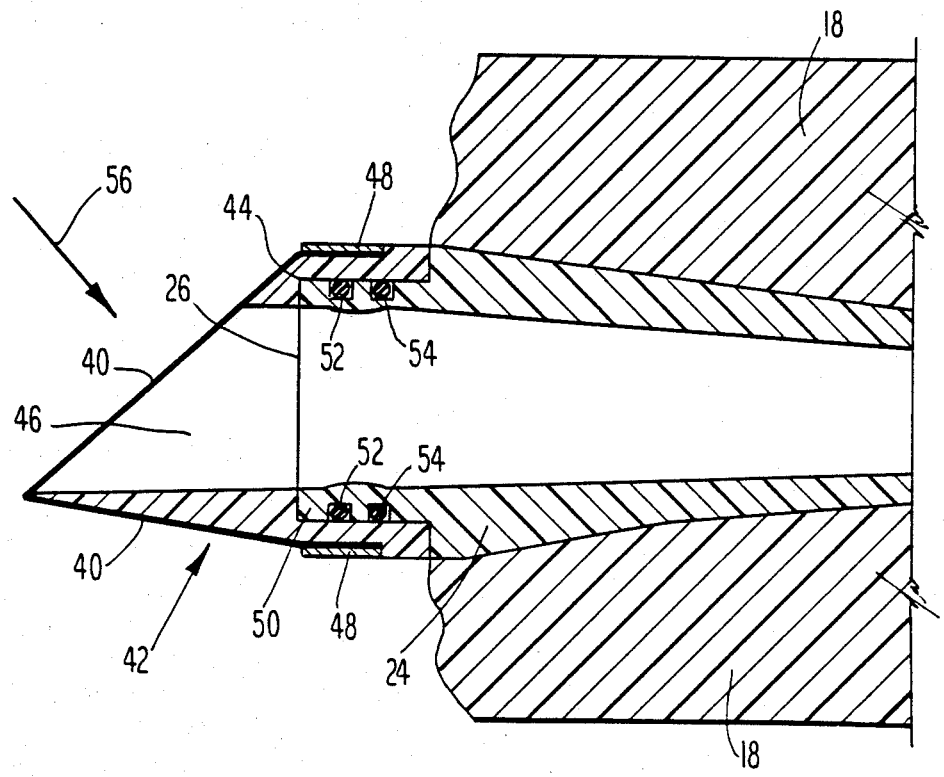
FIG. 2 is a cross-sectional view of the larynx of FIG. 1 taken along section lines 2—2 illustrating the acoustic horn and an improved saliva barrier.

Referring now to FIG. 2, the saliva barrier cartridge, as well as the details of its attachment to the mouth 26 of the horn 24 will be described. As shown in FIG. 2, the microporous saliva barrier 40 is part of an overall saliva barrier cartridge shown generally at 42. The cartridge 42 includes a mounting 44 which is preferably a truncated conical structure, having a central opening 46 therein. The saliva barrier membrane 40 is affixed to the mounting 44 by means of an O-ring 48, which tightly engages the outer surface of the mounting and compresses the membrane 40 against it. The entire saliva barrier cartridge 42 is removably attached to the mouth 26 of the horn 24. The external end of the horn 24 includes a region 50 of reduced diameter which mates with the central opening 46 of the mounting 44. The region 50 of reduced diameter includes a pair of peripheral grooves in which 0-rings 52 and 54 are provided to maintain the cartridge 42 in frictional engagement with the horn 24 and further to preclude penetration of saliva to the interior of the horn 24.

From FIG. 2, it will be seen that the external opening of the mounting 44 is formed on a bias to the longitudinal axis thereof, such that the central opening 46 of the mounting is elliptical in cross-section when viewed from a direction normal to the saliva barrier surface as shown at arrow 56. It has been found that the provision of an elliptical opening to the horn 24 increases speaker volume. It has further been found that the rotational orientation of that elliptical opening further effects speaker volume. Since the mounting 44 is rotatable about its longitudinal axis even when engaged with the horn 24, the user of the larynx 10 may vary the angular orientation of the saliva barrier 40 so as to maximize speaker volume.

Figure 3:
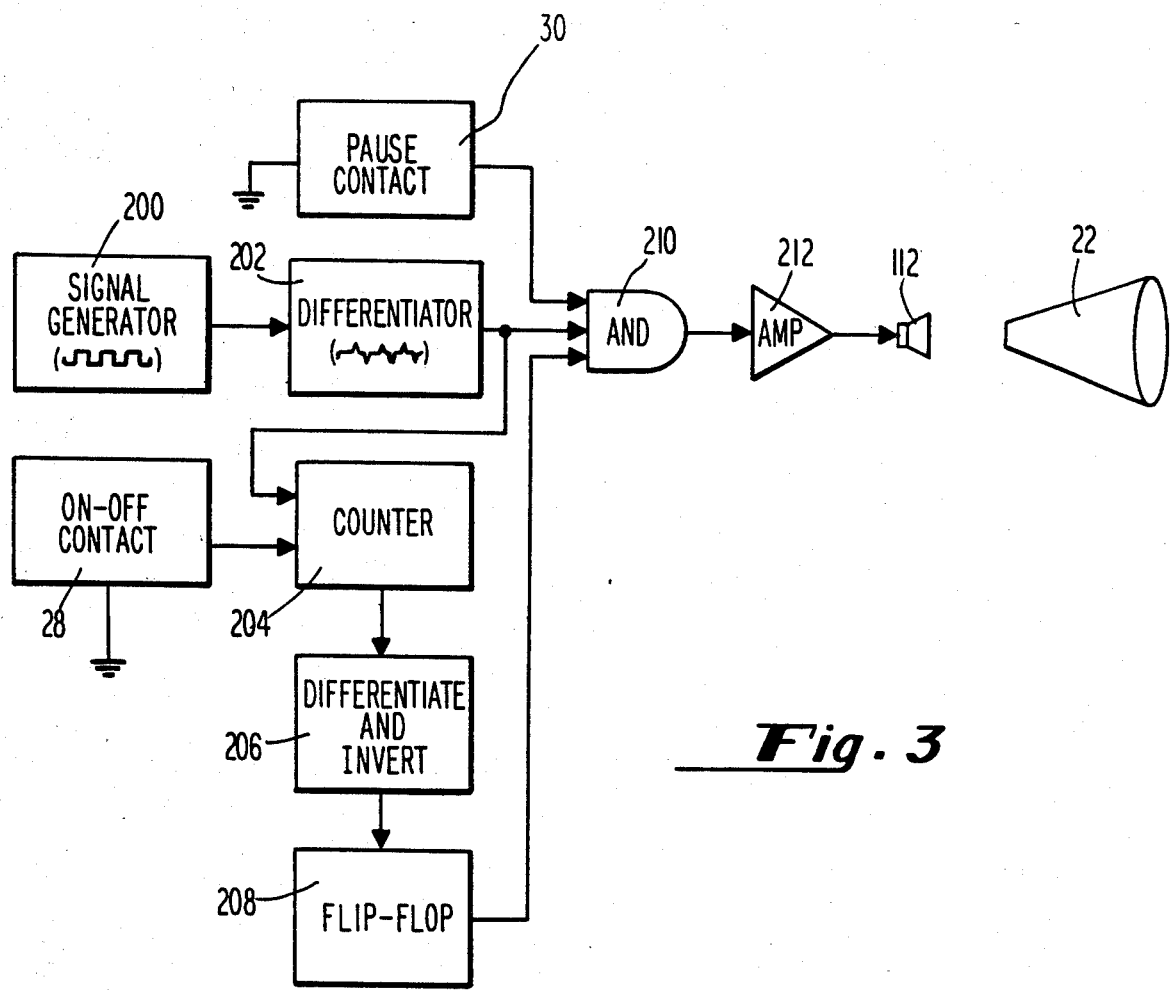
FIG. 3 is a block diagram illustrating the operative electrical components of the preferred embodiment of the artificial larynx of the present invention.
Figure 4:
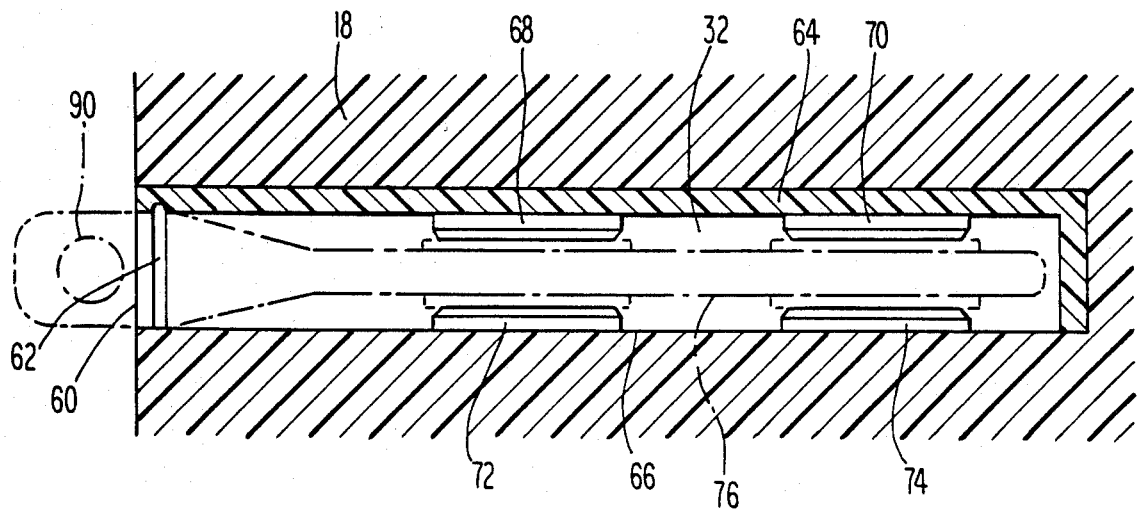
FIG. 4 is a cross-sectional view of the artificial larynx of FIG. 1 taken along section lines 4—4.

FIG. 3 provides further information concerning the operation of the preferred embodiment larynx 10 of the present invention. As shown in FIG. 3, the signal generation circuitry of the present invention is seen to comprise a signal generator 200 and differentiator 202. In the preferred embodiment, a square wave signal generator is utilized, the resultant signal of which is differentiated to produce an output signal comprising a plurality of spikes which are separated by long, near-zero voltage time periods. In the preferred embodiment, the square wave signal generator comprises an astable multivibrator which generates a signal having a frequency between zero and 20 kHz, preferably 60–120 Hz. By differentiating the signal generator output, the frequency and maximum amplitudes of the positive and negatives spikes produced thereby will, of course, correspond to the frequency and amplitude of the square wave signal. The periods of return to near-zero voltage between spikes of the differentiated signal are too short to be audibly resolved, and thus, "audio flicker" is created when the output signal is fed to audio amplifier 212 to produce the output tone of the larynx. Thus, the amplitude and frequency of the apparent sound produced by the larynx has not been changed, while the duty cycle, and thus the power drain of the output signal has been substantially reduced. A duty cycle control means is thus provided which is utilized to reduce the duty cycle of the output of the signal generation means by profitably utilizing the audio flicker effect. In the preferred embodiment, the duty cycle of the signal generation means is at least less than 10 percent, generally less than 5 percent, and most preferably less than about 1 percent. In fact, good results have been obtained using a duty cycle of about 0.85 percent.

The preferred embodiment artificial larynx 10 further comprises a tongue activatable intra-oral switching device. This switching device comprises an ON-OFF circuit for activating or deactivating the device. This selective enabling and disabling function is accomplished by providing at timing means for timing the closure of the switch, which, in the preferred embodiment, is accomplished by completion of a ground path through switches 28 or 30. The desired grounding may be accomplished by bridging between adjacent contacts with the tongue or by activating a sealed switch to bridge these contacts. In this embodiment, counter 204 counts in response to the output of the signal generation means when the ON-OFF switch 28 is grounded, but is inhibited from counting when the ON-OFF contacts are not grounded. In order to turn on the artificial larynx 10 the tongue is held against "ON-OFF" switch 28 until counter 204 has been permitted to count for a preselected period of time, after which an output pulse is provided to differentiator and inverter 206. The output pulse of counter 204 is thus differentiated and inverted in 206 in order to provide a distinct output to bistable multivibrator (flip-flop) device 208, which is caused to assume its "ON" position. When in this position, flip-flop 208 provides a high level signal to "AND" gate 210, then the differentiated output of the high signal generator 200 will be permitted to pass to high gain amplifier 212 and thereafter to speaker 22. When the user hears the signal from speaker 22, the tongue may be removed from ON-OFF switch 28, and the flip-flop 208 will remain in its "ON" position.

In accordance with copending applications Ser. No. 547,753, filed Nov. 1, 1983 and Ser. No. 547,777, filed Nov. 1, 1983 an improved battery pack for powering the circuit of FIG. 3 will be described in detail. As shown in FIGS. 4 through 7, the battery pack is removably and slideably mounted in the power source compartment 32. The power source compartment 32 comprises a cavity formed in the body 18 of the prosthesis 12. Entry to the battery compartment 32 is by way of an opening 60 having a slight depression or lip 67 around the periphery thereof. The battery compartment 32 is formed in part by means of a battery compartment cover 64 which is embedded within the encapsulation material forming the body 18 of the prosthesis 12. The compartment cover 64 forms the walls and top of the battery compartment 32. The floor 66 of the compartment, however, is formed directly of the encapsulation material of the body 18 of the prosthesis. Fixedly attached to the undersurface of the compartment cover 44 are anode contacts 68 and 70. Situated on the floor 66 of the compartment 32 are cathode contacts 72 and 74. When the batteries powering the larynx are in place, the anodes of the batteries are in ohmic contact with anode contacts 68 and 70 while the cathodes are in ohmic contact with the cathode contacts 72 and 74, respectively. The contacts 68, 70, 72 and 74 are, of course, electrically connected to the circuitry described above.

Figure 5:
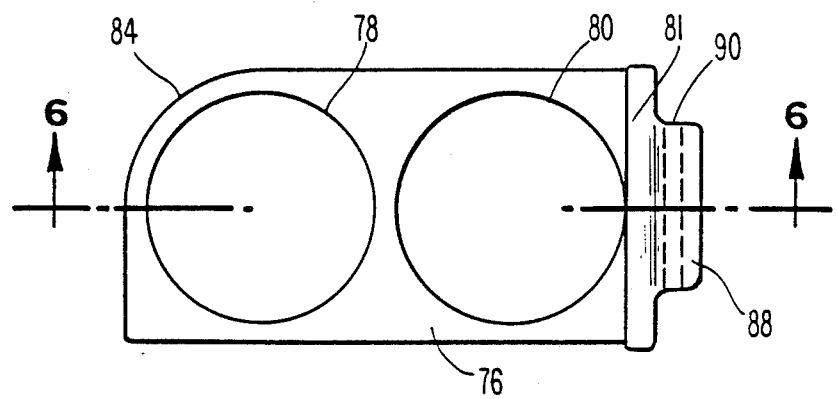
FIG. 5 is a top view of a power source carrier for the power source of the larynx of FIG. 1, the carrier being slideably engageable with the prosthesis shown in that figure.
Figure 6:
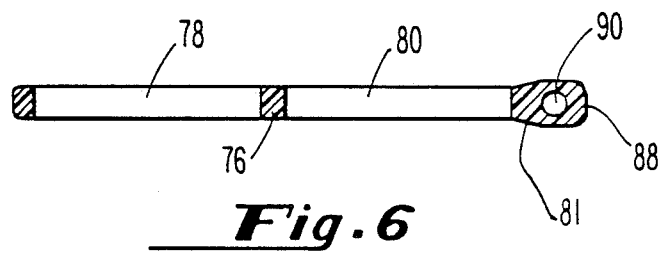
FIG. 6 is a cross-sectional view of the carrier of FIG. 5 taken along section lines 6—6.

In accordance with the preferred embodiment of the present invention, the batteries are inserted within the battery compartment 32, while affixed to a carrier shown in FIGS. 5 and 6. The carrier 76 is slideably and removably received within the compartment 32. The carrier 76 is formed in the shape of a relatively flat panel having apertures 78 and 80 formed therein. Situated within each of the apertures 78 and 80 are two batteries in side-by-side relationship. As mentioned above, such batteries are of the lithium, silver oxide or nickel cadmium (rechargeable) type. The carrier 76 is formed of an electrically insulating material so as to electrically isolate each battery from the other. Preferably, the carrier 76 is formed of a molded silicone. When in place, the anodes and cathodes of the batteries project slightly above the planar surfaces of the carrier 76 so as to contact the anode contacts 68 and 70 and the cathode contacts 72 and 74 mentioned above.

In accordance with the preferred embodiment of the present invention, the carrier 76 includes an integral sealing portion 80 which mates with the lip 62 around the opening 60 to the battery compartment 32 so as to isolate the interior of the compartment from saliva in the intra-oral cavity. In the particularly preferred embodiment, the sealing portion 80 comprises a beveled edge which frictionally engages and mates with the lip 62 to form an extremely watertight seal between the interior of the battery compartment and the exterior thereof. The carrier 76 includes a means for ensuring that the batteries, when mounted in the compartment 32, are oriented such that they have the correct polarity alignment. This is accomplished by the provision of the rounded portion 84 at the leading edge of the carrier 76. As may be seen from FIG. 1, the battery compartment 32 has a corresponding curved edge 86 as shown. For this reason, both the carrier 76 and the compartment 32 are asymmetric. In this manner, complete engagement between the carrier 76 and the compartment 32 is only achievable in one and only one orientation. This feature ensures that power sources mounted in the battery compartment 32 always have the correct polarity alignment.

A means is also preferably provided for easy insertion and removal of the battery pack of the present invention. This means preferably comprises a reinforced handle portion 88 which projects from the opening 60 of the battery compartment 32 when the carrier 76 is in place. The handle portion 88 further includes a transverse bore 90. The bore or hole 90 mates with a gripping means which assists in the insertion or removal of the carrier 76 from the compartment 32.

Figure 7:
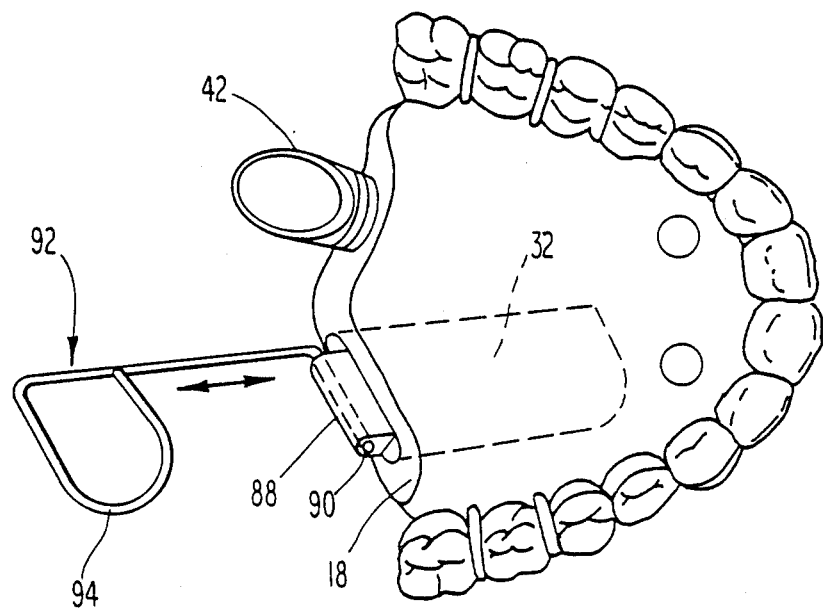
FIG. 7 is a diagrammatic perspective view showing the removal of the carrier of FIG. 5 from the prosthesis of FIG. 1.

As may best be seen in FIG. 7, this gripping means 92 may include a loop portion 94 for finger engagement and a hook portion for engagement with the bore of the handle portion 88 of the carrier 76. As shown in FIG. 7, the gripping means 92 may be used both to insert and to extract the power source and carrier 76 from the battery compartment 32.

While a particular embodiment of the present invention has been shown and described, it will be appreciated that other embodiments will occur to persons skilled in the art, and accordingly, all such embodiments are within the spirit and scope of the appended claims.

What is claimed is:

1. An intra-oral artificial larynx comprising:
   prosthetic means for mounting said larynx within the intra-oral cavity;
   signal generation means mounted on said prosthetic means for generating a preselected electrical signal;
   speaker means mounted on said prosthetic means for converting said signal into acoustic energy;
   a horn having an input opening coupled to said speaker means for acoustically amplifying the output of said speaker means, said horn also having an output opening;
   a mounting removably mounted to said output opening and having a microporous membrane fixed thereto for precluding the penetration of saliva into said horn;
   a tongue activatable switch for enabling said signal generation means and said speaker means; and
   a power source for said signal generation means and said speaker means.

2. A removable saliva barrier for an intra-oral artificial larynx of the type having
   a prosthetic means for mounting said larynx within the intra-oral cavity;
   a signal generation means mounted on said prosthetic means for generating a preselected electrical signal;
   a speaker means mounted on said prosthetic means for converting said signal into acoustic energy;

a horn having an input opening coupled to said speaker means for acoustically amplifying the output of said speaker means, said horn also having an output opening;

a tongue activatable switch for enabling said signal generation means and said speaker means; and a power source for said signal generation means and said speaker means; said barrier comprising:

a microporous membrane; and a mounting, said membrane being fixed thereto, said membrane and said mounting being removably mounted to the output opening of said horn.

3. An intra-oral artificial larynx comprising:

prosthetic means for mounting said larynx within the intra-oral cavity;

signal generation means mounted on said prosthetic means for generating a preselected electrical signal;

speaker means mounted on said prosthetic means for converting said signal into acoustic energy;

a horn having an input opening coupled to said speaker means for acoustically amplifying the output of said speaker means, said horn also having an output opening;

a saliva barrier cartridge for precluding the penetration of saliva into said horn, said cartridge being removably mounted to said output opening, said cartridge including:

a mounting having a central opening therein in acoustic communication with the output opening of said horn, and a microporous membrane sealing said central opening;

a tongue activatable switch for enabling said signal generation means and said speaker means; and a power source for said signal genration means and said speaker means.

* * * * *